United States Patent [19]

Del Mar

[11] Patent Number: 4,720,093
[45] Date of Patent: Jan. 19, 1988

[54] STRESS TEST EXERCISE DEVICE

[75] Inventor: Bruce E. Del Mar, Laguna Beach, Calif.

[73] Assignee: Del Mar Avionics, Irvine, Calif.

[21] Appl. No.: 671,628

[22] Filed: Nov. 15, 1984

Related U.S. Application Data

[63] Continuation-in-part of Ser. No. 621,844, Jun. 18, 1984, abandoned.

[51] Int. Cl.$^4$ .............................................. A63B 1/00
[52] U.S. Cl. ........................................ 272/70; 272/69; 272/128; 272/DIG. 9
[58] Field of Search .................. 272/93, 94, 96, 97, 272/69, 70, 70.2, 73, 118, 128, 129, 130, 131-139, DIG. 9, DIG. 6; 128/25 R, 25 B; 73/379-381

[56] References Cited

U.S. PATENT DOCUMENTS

| | | | |
|---|---|---|---|
| 326,247 | 9/1885 | Root | 128/25 R |
| 964,898 | 7/1910 | Budingen | 128/25 R |
| 1,899,255 | 2/1933 | Bell | 128/25 R |
| 3,592,466 | 7/1971 | Parsons | 272/69 |
| 3,638,940 | 2/1972 | Mehaulic | 272/70 |
| 3,704,886 | 12/1972 | Kay et al. | 272/73 |
| 3,747,924 | 7/1973 | Champoux | 272/70 X |
| 3,824,994 | 7/1974 | Soderberg, Sr. | 128/25 R |
| 3,970,302 | 7/1976 | McFee | 272/130 |
| 3,995,491 | 12/1976 | Wolfla, II | 272/73 |
| 4,470,597 | 9/1984 | McFee | 272/128 |

Primary Examiner—Richard J. Apley
Assistant Examiner—John L. Welsh
Attorney, Agent, or Firm—Bruce D. Jimerson; Daniel L. Dawes; W. Douglas English

[57] ABSTRACT

The specification discloses a self propelled stress testing apparatus for providing graded levels of exercise and for measuring human energy output. An adjustable frictional load calibrated in terms of patient weight and operatively coupled to a pair of translational platforms provides the exercising drag force to a flywheel against which the effort of the user is applied. Reciprocal exercising motion applied to the translational platforms is converted into rotary motion via a pair of unidirectional sprockets. Alternative embodiments employing bifilar and elastically centered slideable guide platform configurations are disclosed as well as special adaptions for use in a weightless space environment.

20 Claims, 16 Drawing Figures

STRESS TEST EXERCISE DEVICE

CROSS REFERENCE TO RELATED APPLICATIONS

This application is a continuation in part of an earlier application entitled "Stress Testing Device" filed June 18, 1984 by Bruce Del Mar as Sole Inventor, Ser. No. 621/844, now abandoned

BACKGROUND OF THE INVENTION

1. Field of the Invention

The present invention relates to a compact self-propelled stress test exercise device which simulates the mechanical action, and work expenditure a subject would experience while climbing stairs. The invention permits the subject to exercise against graded levels of resistance scaled to the subject's own weight, and applied to a friction belt which rides in contact with a flywheel. Output energy is proportional to the rate at which the subject climbs within the device as well as the weight of the subject.

2. Description of the Prior Art

Numerous devices have been marketed for the purpose of providing graded levels of exercise as a means toward evaluating the physiological condition of a patient, in particular the cardiovascular performance of a patient, during application, and immediately following application of the exercise. One commonly used exercise apparatus for such stress testing is the electric treadmill which consists of an elongated platform of rollers over which an endless belt is driven by an electric motor. Such a device is described in U.S. Pat. No. 3,703,284 entitled "Diagnostic and Therapeutic Exercise Treadmill". In using such apparatus, the patient must continue to pace himself so as to "keep-up" with the speed of the endless belt. The starting and stopping of such devices can be dangerous, and the clinical operator must constantly and alertly monitor the patient to prevent accidents. Although several protective arrangements have been utilized, as for example those described in U.S. Pat. No. 3,711,812 entitled, "Drive and Control Systems for Diagnostic and Therapeutic Exercise Treadmill", treadmills nevertheless remain potentially dangerous even though adequate precautions are taken. What is actually desired is a compact, simple, safe exercising device which will provide the work loading necessary for a submaximal stress test of a person's cardiovascular system comparable between persons of various weights with all the energy generated by the patient functioning as the sole prime mover.

Accordingly, a primary object of the present invention is to provide a safe self-propelled stress test exercise device which is simple to build and operate, and which gives comparable test results between patients of varying body weight.

A further object of the invention is to provide a stress test exercise device which will simulate a common activity so as to provide exercise to achieve high heart rates together with an accurate indication of both the instantaneous and cummulative energy delivered by the patient while engaging in the activity.

Although some attempts have been made to ameliorate the problems associated with traditional treadmills, these devices have in turn created other problems. In U.S. Pat. No. 3,826,491 entitled "Exercise Treadmill" the treadmill is elevated at one end to simulate an inclined walking surface. Such devices however can create problems at high inclination angles - and sufficient friction must be maintained with respect to the drive system to preclude the possibility of undesirable belt movement under such conditions.

Another shortcoming of traditional externally powered stress test exercise devices lies in the fact that the forces over which body energy is measured are not well defined for purposes of determining power output. It is well known for example that the efficiency of a muscle is dependent upon the nature of the imposed load. Thus, a pure resistive force theoretically produces no energy output until there is movement—yet such forces rapidly tire the muscle as a result of the body energy expended in maintaining a counter force. It is therefore desirable that the human output from any self-powered exercise device be related to measurable energy units, and that the measurable quantities be indicative of the physiological output. Moreover, the physiological effort should not rapidly deplete the muscles used to maintain the output—i.e., the effort should involve a large muscle mass in such a way that the muscles function in their usual manner to carry out a common or representative activity over an extended period of time.

Accordingly, a further object of the invention is to provide a stress test exercise device for measuring sustained physiological energy output.

Another object of the invention is to provide a stress test exercise device which functions to provide relatively consistent correlations between the physiological energy dissipated and the measurable mechanical energy outputted.

Although traditional self-powered stress test exercise devices such as stationary bicycles and rowing machines are partially effective for accomplishing the above objectives, they have some complications in terms of their capability of establishing comparable stress loadings between patients of various limb lengths and body weights. Self propelled and motor actuated bicycle ergometers have been used to apply various stages of work loading for physiological stress testing but they have the disadvantage of using muscle motion few people are prepared to carry to the required energy levels and they do not provide a simple correlation of results by loadings calibrated to body weight. What is actually desired is a device which will accurately and consistently provide useful, comparable stress test exercise for patients of various body weights, independent of varient styles of use and immune to variations for all users, accordingly:

A further object of the invention is to provide a self-powered stress testing device wherein the stress test loading is at graded levels proportional to the weight of the patient and substantially independent of the method or style of use.

Another object of the invention is to provide a safe self-powered stress test exercise loading apparatus which will facilitate the measurement of energy output while the patient performs a simulated common activity such as climbing stairs without gaining sufficient height to be injured by a fall.

Another object of the invention is to provide a self-powered stress test exercise device which can be easily switched from one level of load to another.

Another object of the invention is to provide a stress test exercise device which may be operated at comparable effective stress rates for all users.

Another object of the invention is to provide a variable resistance load which can be applied by either weights or springs or both in earth's gravity or outside of it.

A further object of the invention is to provide a stress test exercise device which can be utilized in a weightless space environment.

Another object of the invention is to provide an elastic suspension arrangement for a self-powered pedal platform exercising device.

Another object of the invention is to provide a visual readout of the cumulative energy expended during a particular time interval.

Another object of the invention is to provide a visual readout of the instantaneous rate at which energy is expended by the operator.

Other objects and advantages of the present invention will be obvious from the detailed description of a preferred embodiment given herein below:

SUMMARY OF THE INVENTION

The aforementioned objects are realized by the present invention which comprises a pair of horizontal platforms; a suspension arrangement which allows each platform to be translated at an inclined angle; a linkage arrangement for interconnecting the platforms so that each platform moves in reciprocal relationship to the other; a flywheel; unidirectional ratchet drives for converting the reciprocal motion of each platform to a unidirectional rotary motion of the flywheel; a friction belt positioned to ride in contact with the rim of the flywheel and a loading means for varying the frictional force exerted by the friction belt upon the flywheel. Both bifilar suspension and slideable guideways are utilized in alternative embodiments to effect parallel plane translation of the platforms. For optimum dynamic performance, the platforms are elastically centered by tension springs.

DETAILED DESCRIPTION OF A PREFERRED EMBODIMENT

Figure 1:
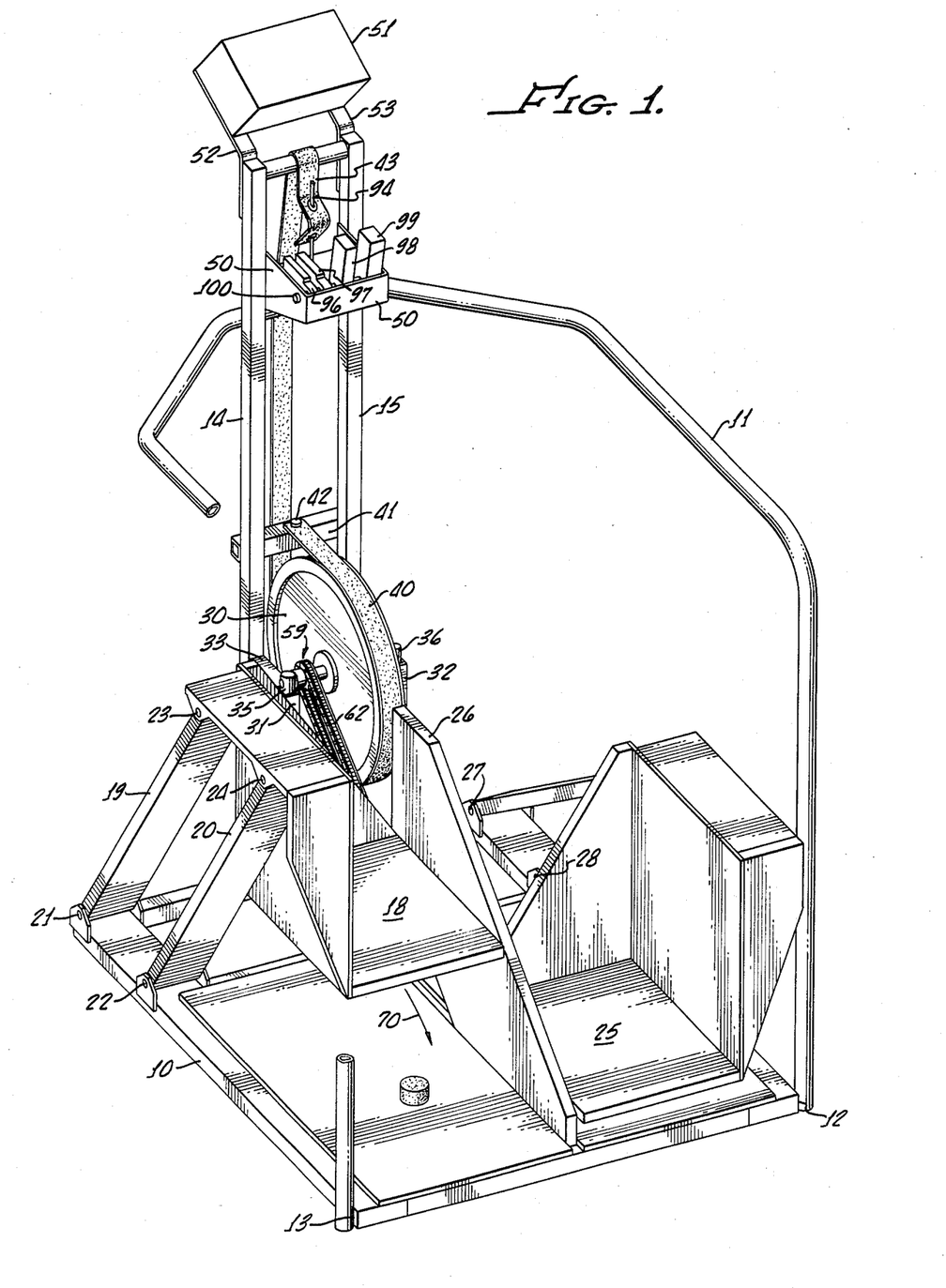
FIG. 1 shows a perspective view of a first preferred embodiment of the invention employing a bifilar platform suspension system.
Figure 2:
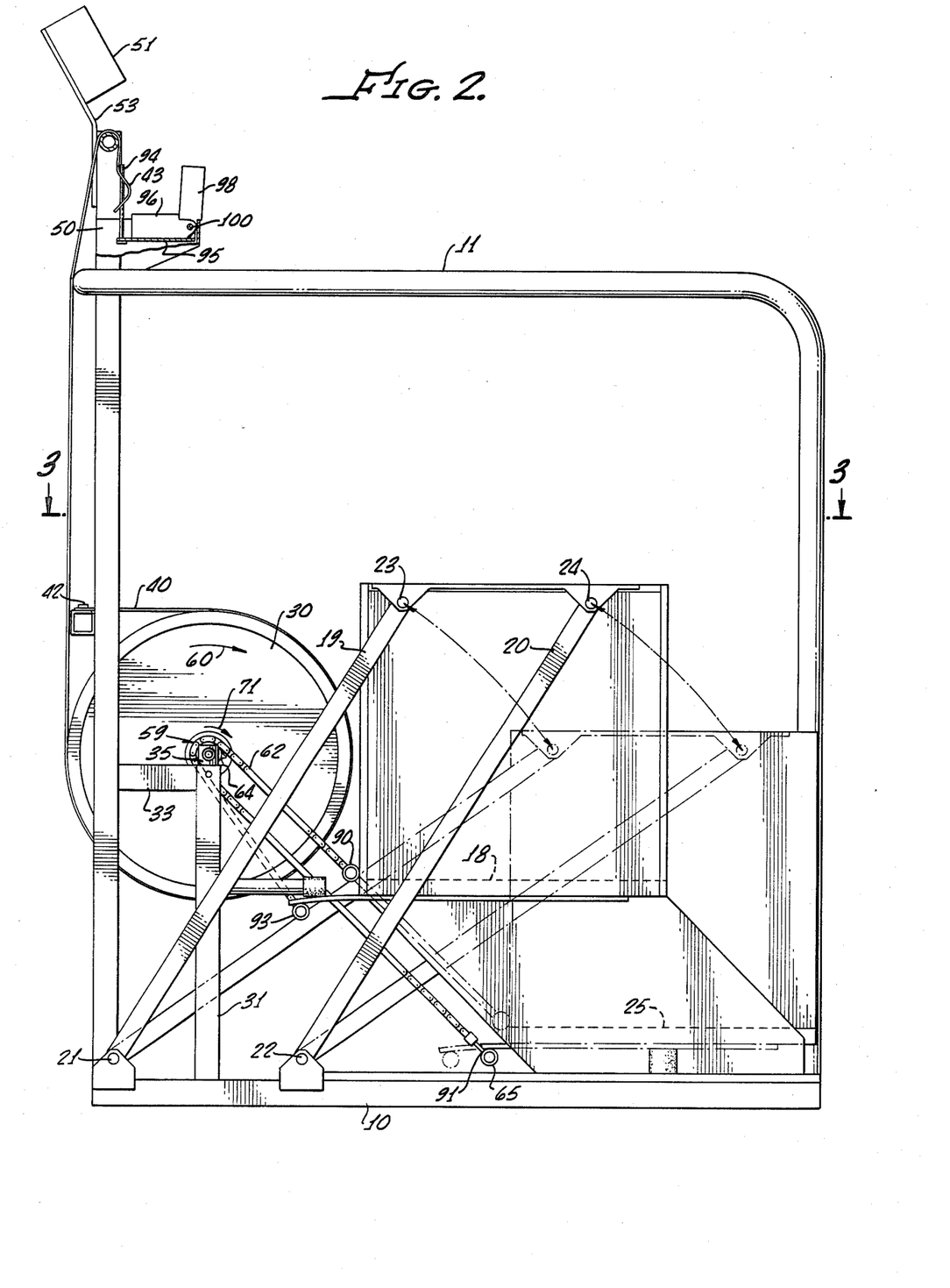
FIG. 2 shows a side elevation of the embodiment shown in FIG. 1.
Figure 3:
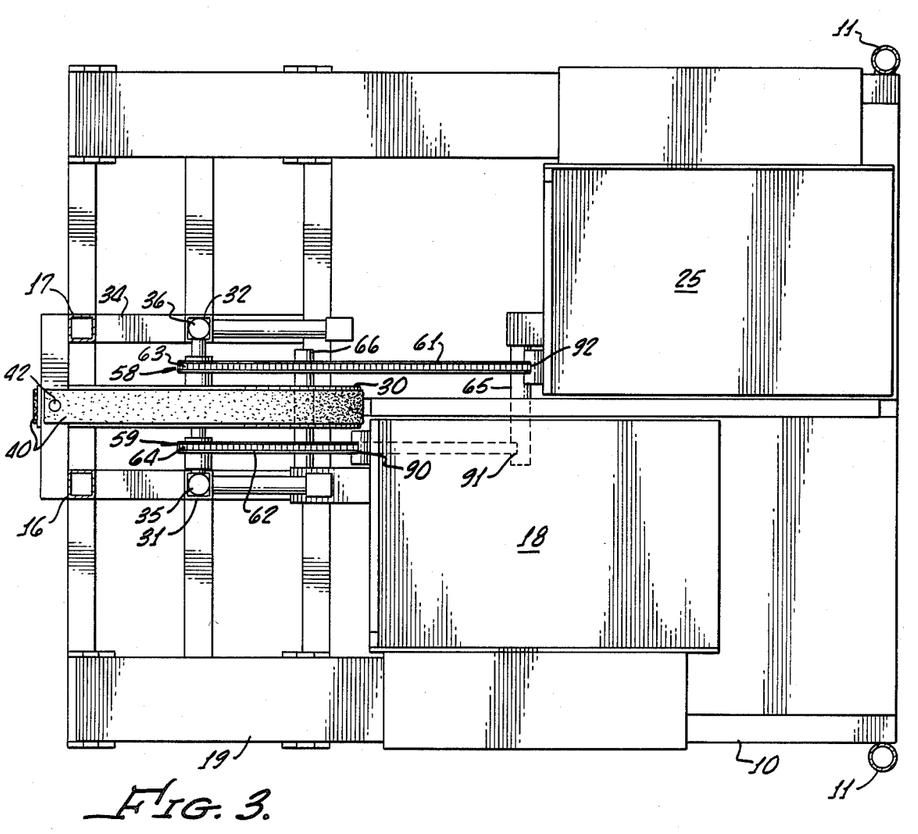
FIG. 3 shows a plan view of the platform and chain drive arrangement of the device illustrated in FIG. 1

Adverting to the drawings and particularly FIGS. 1, 2, and 3, there is shown a base platform 10; a handrail support 11 attached to said base at the points 12 and 13; a pair of upright members 14 and 15 attached to base platform 10 at 16 and 17 respectively; a left pedal platform 18 bifilar mounted to translate at an inclined angle in accordance with the functional operation of the left bifilar suspension comprising links 19 and 20 each journal mounted to base platform 10 at 21 and 22 and left pedal platform 18 at 23 and 24; a right pedal platform 25 bifilar suspended to translate at the same angle of inclination as left pedal platform 18, said right bifilar suspension system comprising links identical to 19 and 20 journaled to the right pedal platform 25 and at corresponding locations 27 and 28 of the base platform 10 so that the left and right halves of the aforementioned recited structure are symetrical with respect to partition wall 26. The translational motions of the right and left pedal platforms 25 and 18 respectively are coupled to a flywheel 30 via chains 61 and 62 and sprockets 58 and 59 which contain internal unidirectional ratchet drives 63 and 64 as more fully described hereinbelow. Upright members 14 and 15 together with vertical struts 31 and 32 and horizontal braces 33 and 34 function as a support frame for flywheel bearings 35 and 36. Flywheel 30 rotates in the direction of arrow 60 whenever the pedal platforms 18 and 25 are operated. Friction belt 40 is attached to cross member 41 at one end by pin 42 and is adapted to ride in contact with the rim of flywheel 30 so as to maintain a frictional force in an amount which is determined by the load applied at end 43 are more fully described hereinbelow. A weight tray assembly 50 is attached between upright members 14 and 15 and a readout display 51 is mounted to the same upright members 14 and 15 by angle brackets 52 and 53.

Left pedal platform 18 and right pedal platform 25 are interconnected by a unique mechanical arrangement comprising chains 61 and 62, unidirectional ratchet sprocket drives 58, 59, 63 and 64, and cross connecting right and left pedal platform arms 65 and 66. As more clearly seen in FIG. 3, one end of chain 62 is attached to left pedal platform 18 at 90 and the other end of chain 62 is attached to right pedal platform arm 65 at 91. Similarly, one end of chain 61 is attached to right pedal platform 25 at 92 and the other end of chain 61 is attached to left pedal platform arm 66 at 93. The operation of the system is as follows: When left pedal platform 18 is operated so as to translate it downwardly along the inclined path determined by the bifilar suspension links 19 and 20 in the direction of arrow 70, sprocket 59 is rotated in the direction of arrow 71. The rotational motion of sprocket 59 is coupled to flywheel 30 via an internal unidirectional ratchet 64 so that flywheel 30 is caused to rotate in the direction of arrow 60. As left pedal platform 18 descends along the inclined path 70, right pedal platform 25 is pulled upwardly by chain 62 via right platform arm 65. Similarly, when right pedal platform 25 is operated to move it downwardly, chain 61 rotates sprocket 58 causing internal ratchet 63 to continue to rotate flywheel 30 in the direction of arrow 60, and left pedal platform 18 is pulled upwardly by chain 61 via left pedal platform arm 66. The left and right platforms 18 and 25 thus move in reciprocal relationship, each functioning to elevate the other and rotate the flywheel 30 in the direction of arrow 60 when a downward force is applied. During the upward assension of either pedal platform 18 or 25 the associated internal sprocket (either 63 or 64) free wheels so that flywheel 30 continues to rotate in the direction of arrow 60. Continued rotation of flywheel 30 is thus maintained by applying a downward force to whichever platform is descending.

Human beings are well adapted to performing certain mechanical tasks such as climbing stairs. The leg and body muscles involved in such an activity function efficiently—that is, the ratio of mechanical work outputted by the body as a whole relative to the rate at which fatigue occurs in the muscles used to deliver the output power is maximized. It will therefore be understood, that for optimum results, the pedal platforms 18 and 25 are preferrably operated to produce complete strokes i.e., the patient will step forward and upward as though climbing stairs to apply his weight to one pedal platform until it descends to the bottom of its stroke at which time he will step forward and upward to lift his weight to the other pedal platform which will have ascended to its apex (top of stroke) and so on. When properly operated as described the output energy will provide an accurate and reliable measure of the internal physiological energy expended.

Figure 4:
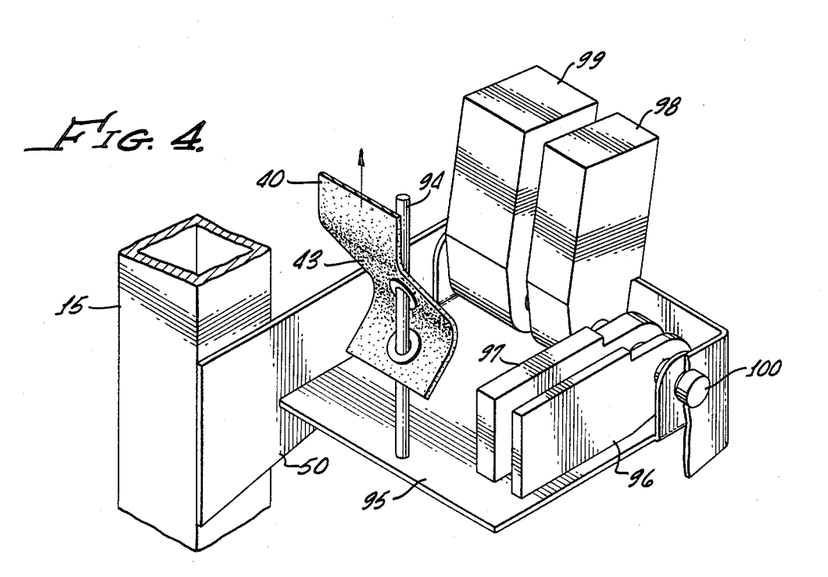
FIG. 4 is a perspective view of the weight tray assembly.

In order to achieve varying workloads, an array of weights are utilized to alter the tension force applied to belt 40. Each weight produces a different frictional force which can be measured to provide correlative calibration of the workload produced. The details of the weight tray assembly 50 are shown in FIG. 4 wherein as seen the strap 40 is adjustable positioned relative to pin 94 so as to support pan 95 horizontally. Pan 95 and weights 96, 97, 98, and 99 are mounted to freely rotate about pin 100. The amount of tension force applied to strap 40 will thus depend upon the position of the weights 96-99 i.e., which weights rest against pan 95. It will be understood that springs or other devices for exerting continuous forces may be used in lieu of weights, and in fact such devices are required where the invention is to be utilized in a weightless space environment.

Figure 5:
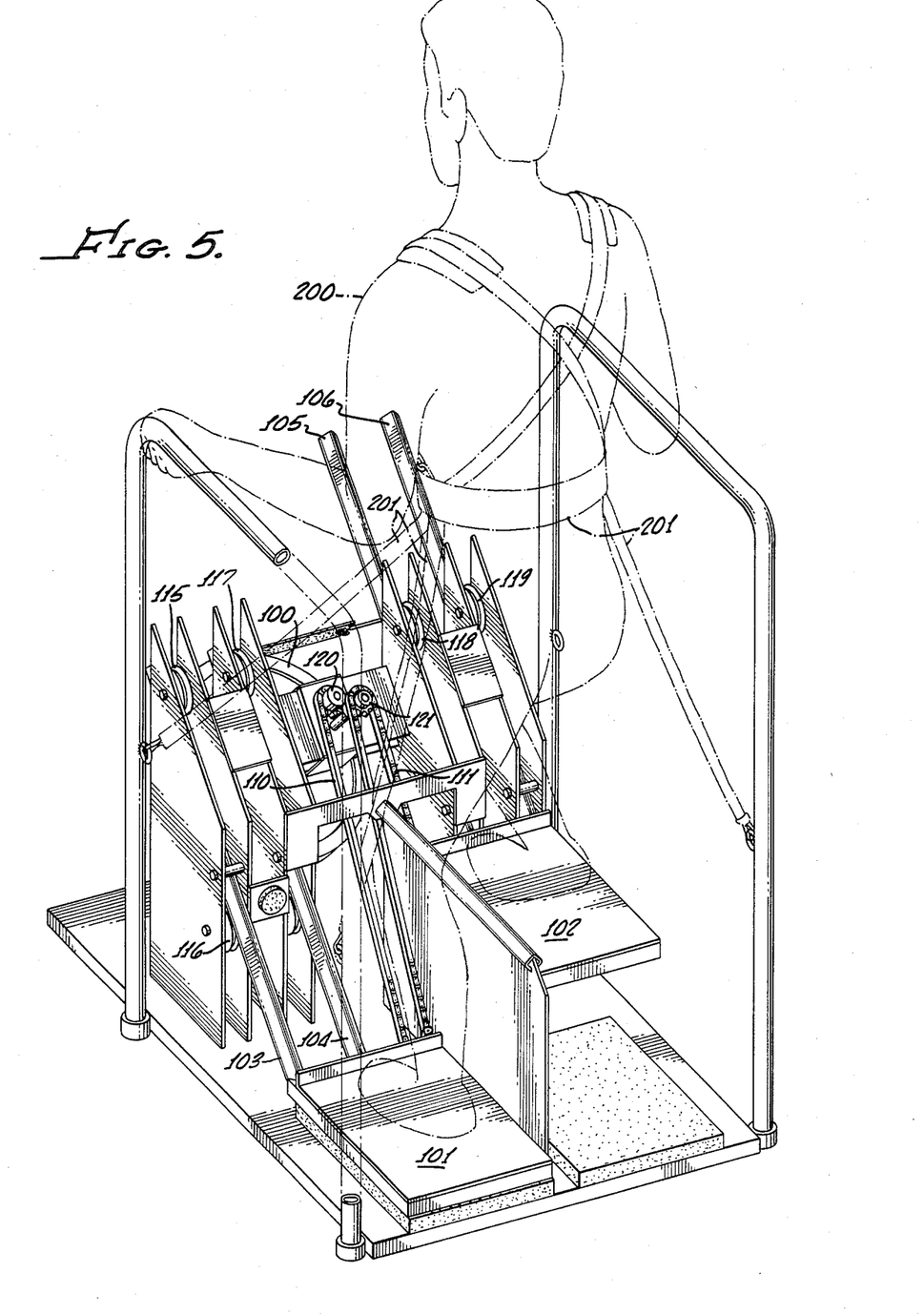
FIG. 5 is a perspective phantom view illustrating the operation of a slideable guideway embodiment of the invention in a weightless environment.
Figure 6:
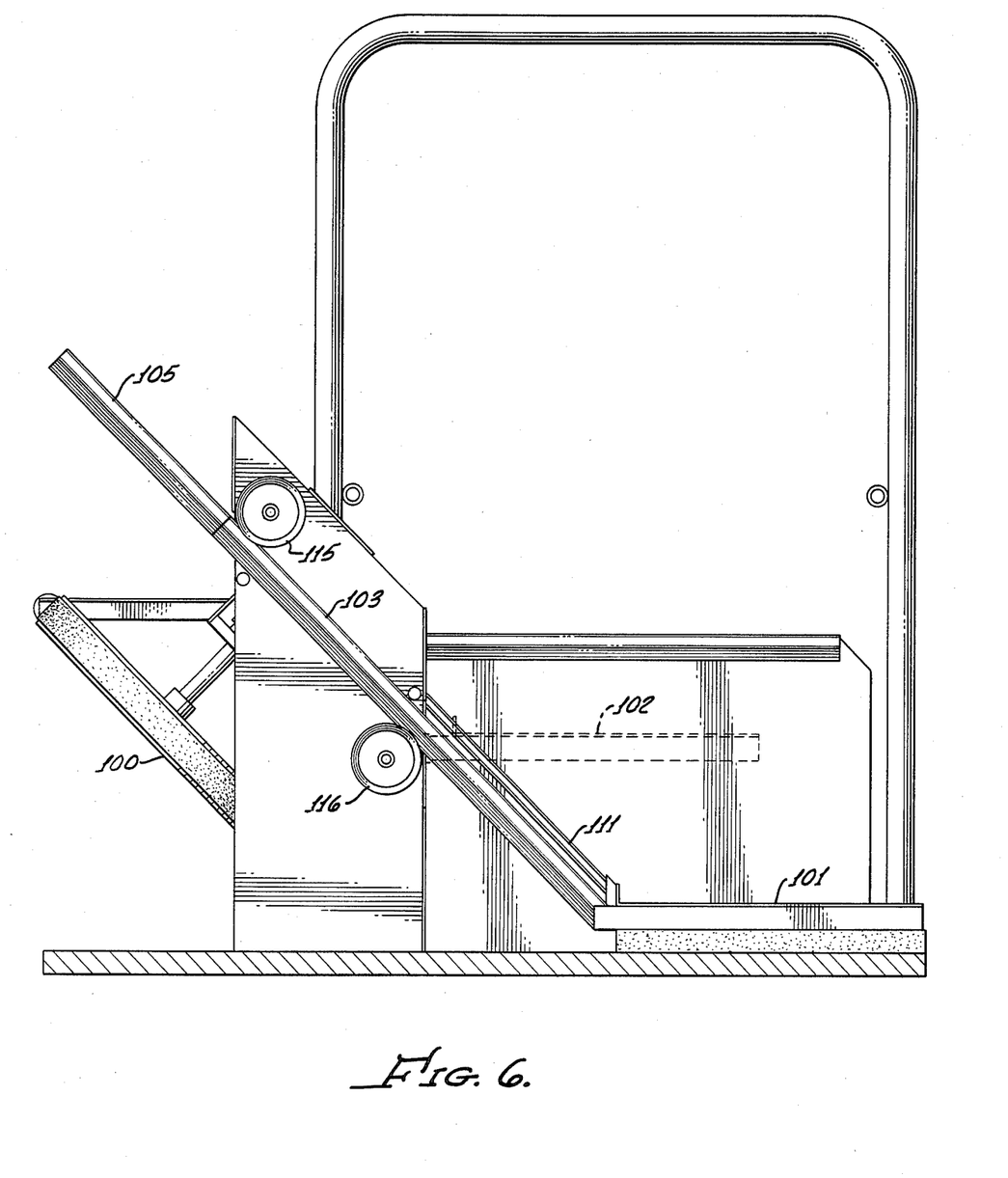
FIG. 6 is a side elevation of the slideable guideway embodiment showing the details of the roller arrangement.
Figure 7:
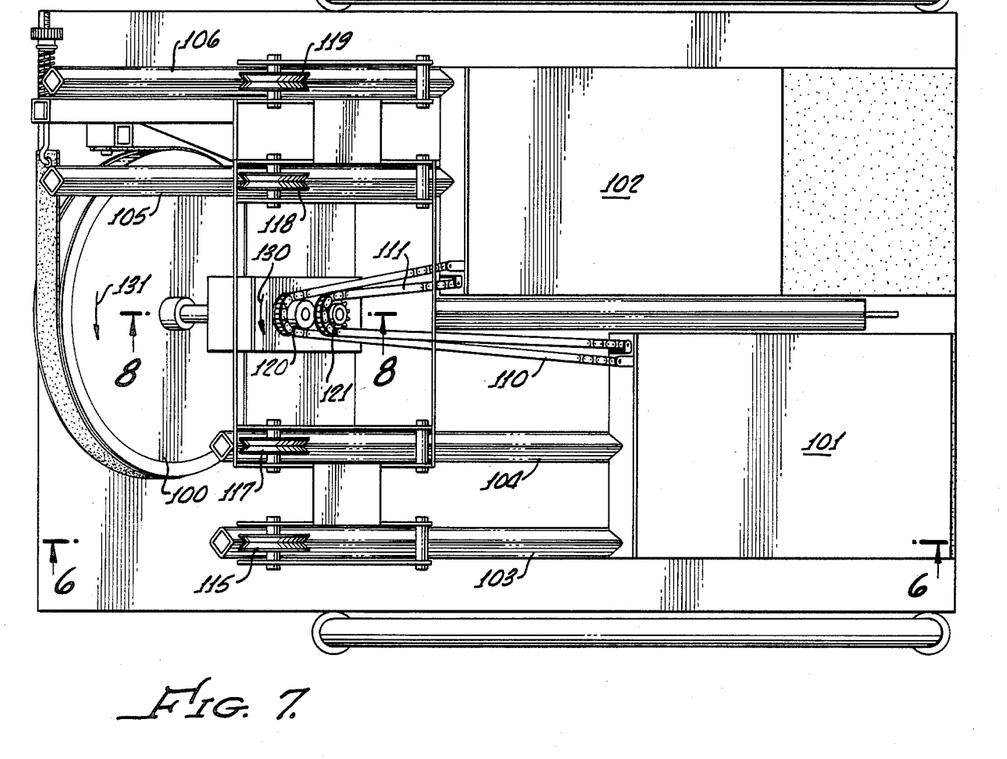
FIG. 7 is a plan view of the platform and drive arrangement of the device illustrated in FIG. 5.

FIGS. 5, 6, and 7 show an alternative embodiment of the invention wherein the flywheel 100 is mounted so as to rotate in a plan parallel to the motion of the pedal platforms 101 and 102. The pedal platforms 101 and 102 are themselves suspended to translate at an inclined angle determined by the relative position of cooperating pairs of pulley wheel guides, each pedal platform 101 and 102 being interconnected by a pair of drive chains 110 and 111 which operate flywheel 100 as more fully described herein below.

Figure 8:
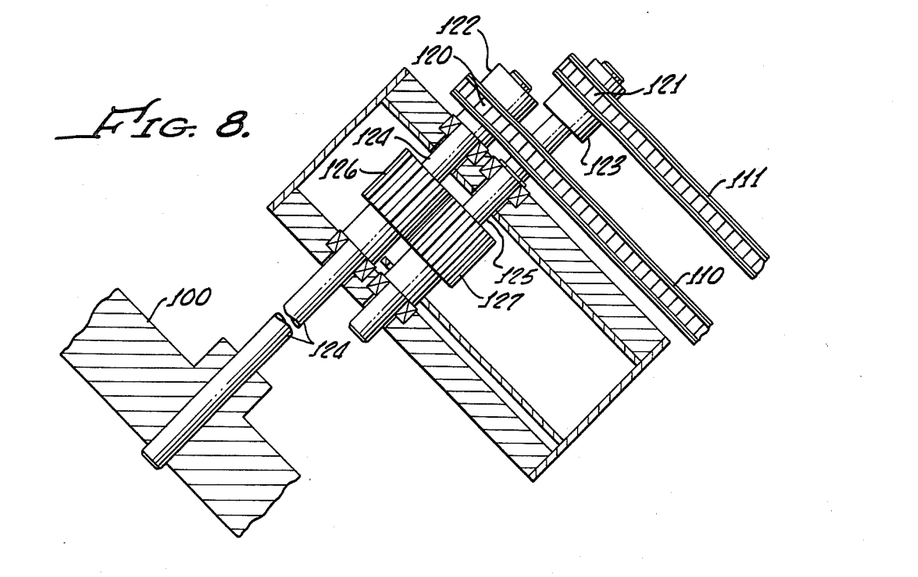
FIG. 8 is a cross section taken through 8—8 of FIG. 7 showing the details of the gear and ratchet arrangement.

Referring to FIG. 6, the translational angle of pedal platform 101 is determined by the position of the top and bottom guide pulley wheel 115 and 116 respectively which ride in contact with the upper and lower "V" shaped surfaces formed by the corners of square bar member 103. Similarly, as shown in FIG. 7, the top pulley wheels 117, 118 and 119 function in the same capacity with respect to corresponding bottom pulley wheels (not shown) to provide guideways for square bar members 104. 105, and 106 respectively. Square bar members 103 and 104 are attached to pedal platform 101 and square bar members 105 and 106 are attached to pedal platform 102. Chain 110 is attached to pedal platform 101 and 102 so as to engage sprocket 120 and chain 111 is attached to pedal platform 101 and 102 so as to engage sprocket 121. As depicted in FIG. 8 each sprocket (120 and 121) contains an internal ratchet (122 and 123 respectively) which functions to facilitate unidirectional drive of the associated output shaft 124 and 125. The unidirectional motion of the output shafts 124 and 125 are "summed" together by gears 126 and 127 so that flywheel 100 always rotates in the same direction. For example, when pedal 101 is descending because of an applied downward force, both sprockets 120 and 121 rotate in the direction of arrow 130. The drive to flywheel 100 is however supplied only by ratchet 122 which causes flywheel 100 to rotate in the direction of arrow 131. During this time interval pedal 102 ascends and sprocket 121 freewheels in the same direction because the pawl of internal ratchet 123 is disengaged. In a like fashion, a downward force applied to pedal 102 causes both sprockets 120 and 121 to rotate in the direction opposite to arrow 130, with power being supplied by internal ratchet 123 so as to rotate flywheel 100 in the direction of arrow 131 via the reversing action of gears 126 and 127. In this situation, the pawl of internal ratchet 122 is disengaged so that sprocket 120 freewheels. Flywheel 100 is thus powered to rotate in the same direction irrespective of the platform to which a force is applied. The structure shown in FIG. 6, 7, and 8 thus constitutes an alternative embodiment of the invention wherein a translational reciprocating linear motion is converted to unidirectional rotary motion.

FIG. 5 shows a harness arrangement which can be employed in a weightless environment, as for example that encountered in a spacecraft. The operator 200 is restrained by the belt harness assembly so as to facilitate the application of an exercising force to the pedal platforms. The belt and harness assembly may also be utilized on earth to increase the rate of physiological energy output over that which can be achieved with only one "g" gravitional environment. For high frictional loads, the rate of generation of output energy would then not be limited by the weight of the operator.

Figure 9:
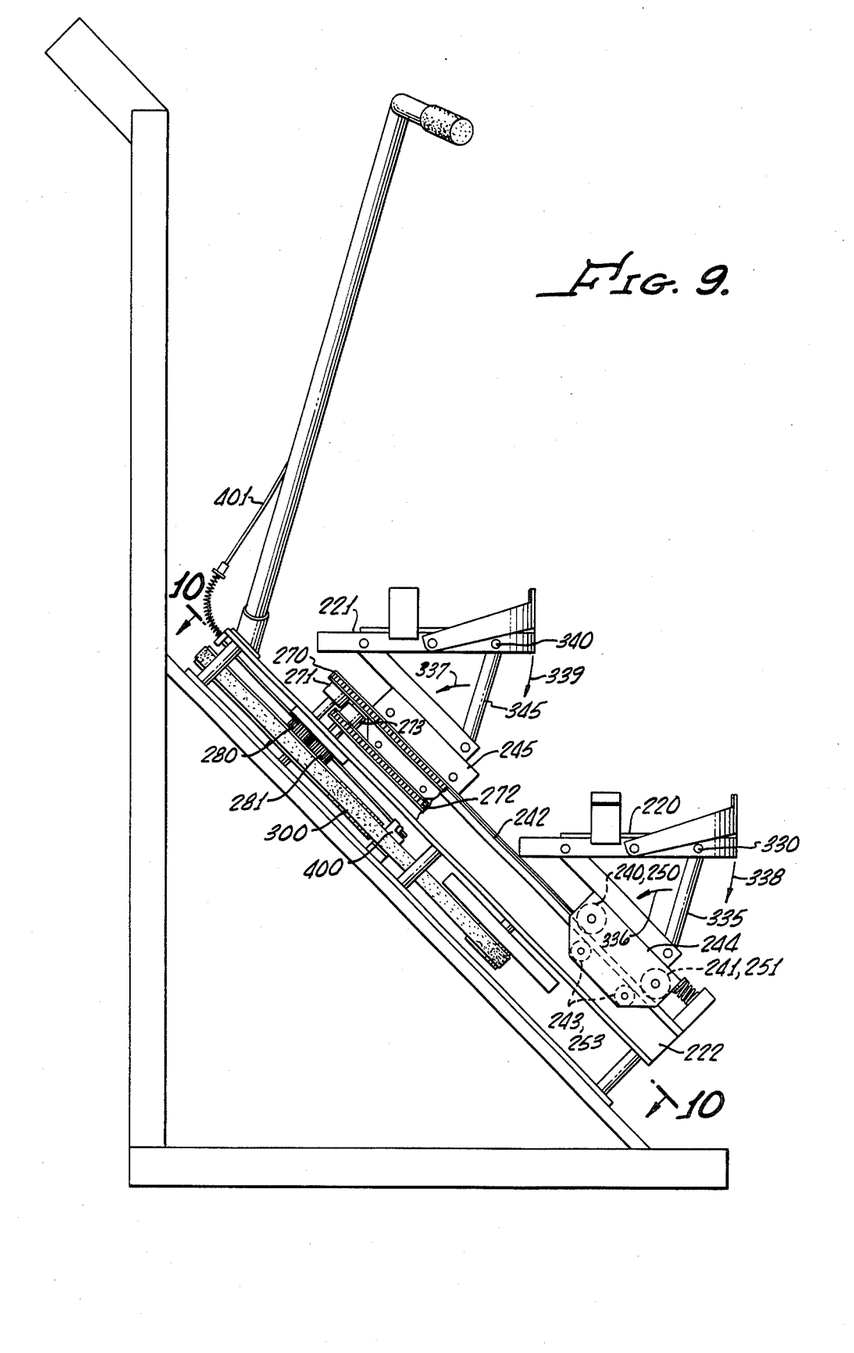
FIG. 9 is a side elevation of a ramp guideway embodiment suitable for a weightless environment.
Figures 10, 11:
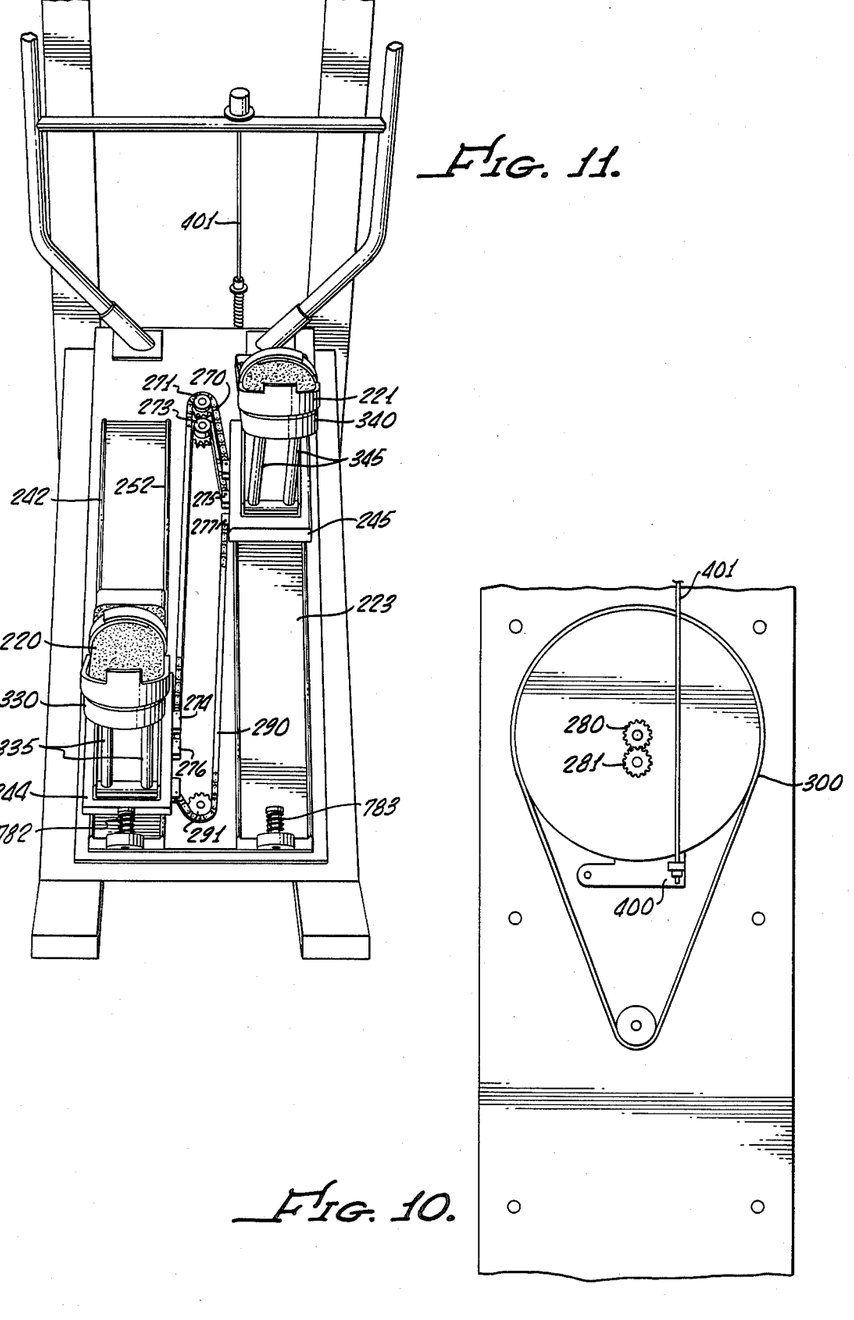
FIG. 10 is a cross section taken through 10—10 of FIG. 9 showing the details of the gear arrangement.
FIG. 11 is a perspective view of the ramp guideway embodiment.
Figure 12:
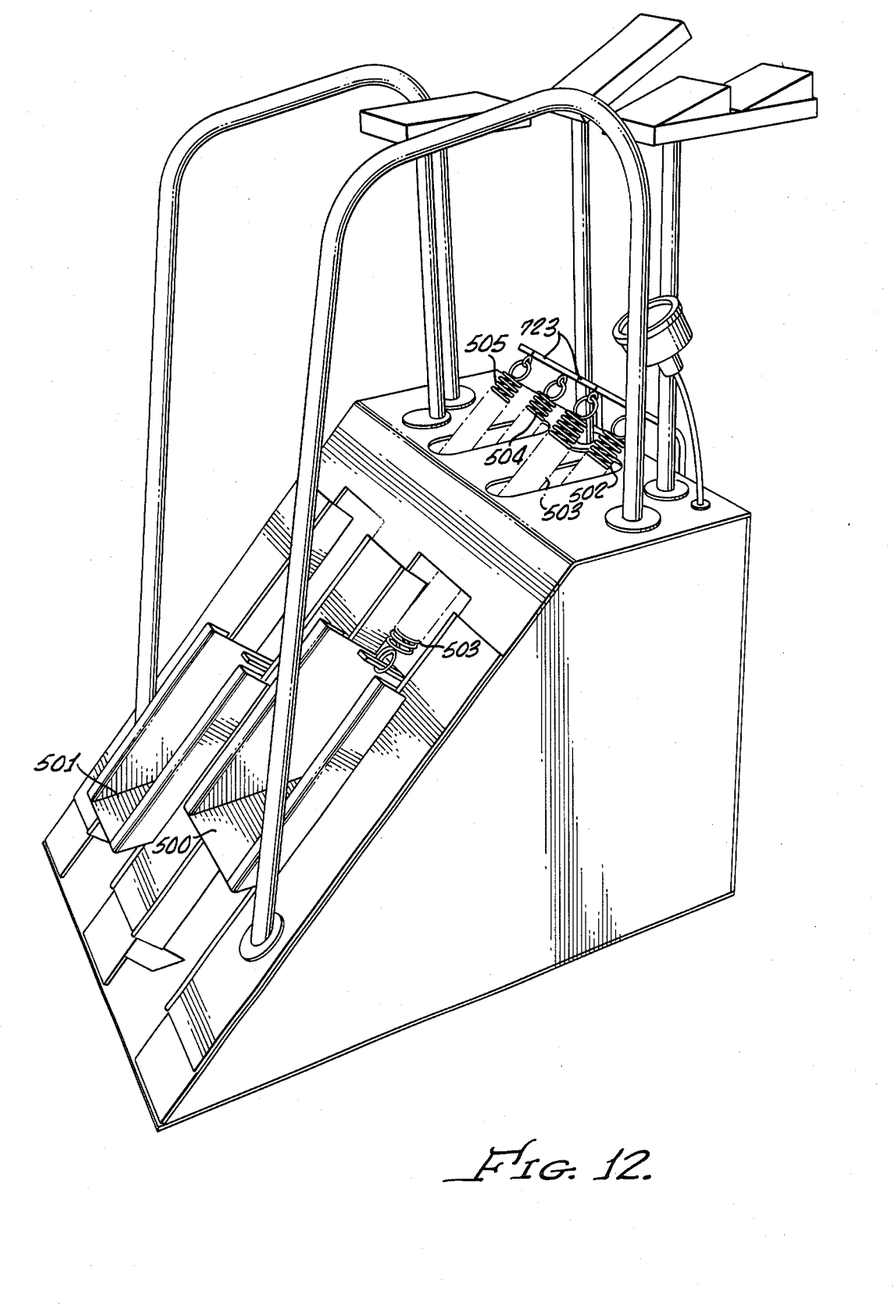
FIG. 12 shows a perspective view of a preferred elastically centered pedal platform embodiment of the invention.

FIGS. 9, 10, and 11 show a preferred adaption of the invention for use in a weightless environment. In this embodiment the pedal platforms 220 and 221 are mounted on cars 244 and 245 which are roller locked to the upper and under lip of a protruding flange. The flange itself is formed as a part of a "U" channel which functions as a guideway for each car, that is "U" channel 222 functions a guideway for car 244 and "U" channel 223 functions as a guideway for car 245. As shown in FIG. 9, the wheel pair 240-250, and wheel pair 241-251 ride on the upper surface of lips 242 and 252 respectively and wheels 243 and 253 ride on the lower surface of lips 242 and 252 respectively so that car 244 remains track bound irrespective of its orientation in a gravitational or non-gravitational field. Car 245 is similarly restrained by correspondingly located wheels.

Chain 270 engages ratchet sprocket 271 and chain 272 engages ratchet sprocket 273. Chain 270 is attached at one end 274 to car 244 and at the other end 275 to car 245. Similarly, chain 272 is attached at one end 276 to car 244 and at the other end 277 to car 245. Ratchet sprockets 271 and 273 together with gears 280 and 281 function in a manner analogous to ratchet sprockets 120-121 and gears 126-127 so as to continuously rotate flywheel 300 in one direction as the pedal platforms 220 and 221 are reciprocated by the action of the operator. The cars 244 and 245 are also linked together via chain 290 which functions in conjunction with idler sprocket 291 to maintain the positional relationship between the cars in a non-gravitational environment. Chain 290 and idler 291 thus prevent car 244 and car 245 from coasting forward simultaneously—an event which would free chains 270 and 272 from their corresponding sprockets 271 and 273. Springs 782 and 783 function to minimize the shock at the limits of travel and to provide a return boost for the reciprocal stroke, it being understood that bungees or other elastic energy storage devices may be used to effect similar results.

A further advantage of the embodiment shown in FIGS. 9, 10, and 11 lies in its portability. The pedal platforms may be folded flat (parallel to the inclined surface) by removing pins 330 and 340 so as to permit links 335 and 345 to rotate in the direction of arrows 336 and 337 and platforms 220-221 to rotate in the direction of arrows 338 and 339. In addition, the embodiment features a friction brake arrangement comprising a shoe 400 which is operated by lever 401 to engage the outer surface of flywheel 300 with sufficient force to restrain rotation.

The aforementioned embodiments are particularly well suited to applications where it is desirable to provide high muscle resistance over an extended period of endeavor. In these embodiments at higher drag loading the weight of operator will not be sufficient to achieve speeds at which the device is to be operated. Consequently, there will be an upper limit to the rate at which energy is expended. In many clinical applications however, it is desirable to provide a range of resistance which does not limit the speed at which the device is operated. Thus we are directed to the following:

FIGS. 12, 13, 14, and 15 show an alternative preferred embodiment of the invention wherein the pedal platforms 500 and 501 are elastically centered by extension springs 502-503 and 504-505 respectively. An important advantage of the preferred embodiment shown in FIGS. 12-15 lies in the fact that the work expended in moving either pedal downwardly (by the application of the user's weight) is stored in the extended springs and partially recovered on the return lift. As a consequence, the system dynamics are improved because of the lifting force produced by the extended springs which effectively decrease the pedal return time. In essence, this allows the operator to increase his energy output under a given load condition; i.e., the effective climbing rate is enhanced, the rate of application of energy is increase, and the heart rate will adjust accordingly. At any given drag loading, the advantage of the improved dynamics are particularly apparent for lightweight persons. Thus, under high load conditions, a lightweight person may be unable to operate the pedals of the previously described embodiments at a speed which will produce a significant increase in heart rate; consequently, an important objective of the device in clinical diagnostics would be lost.

Figures 13, 16:
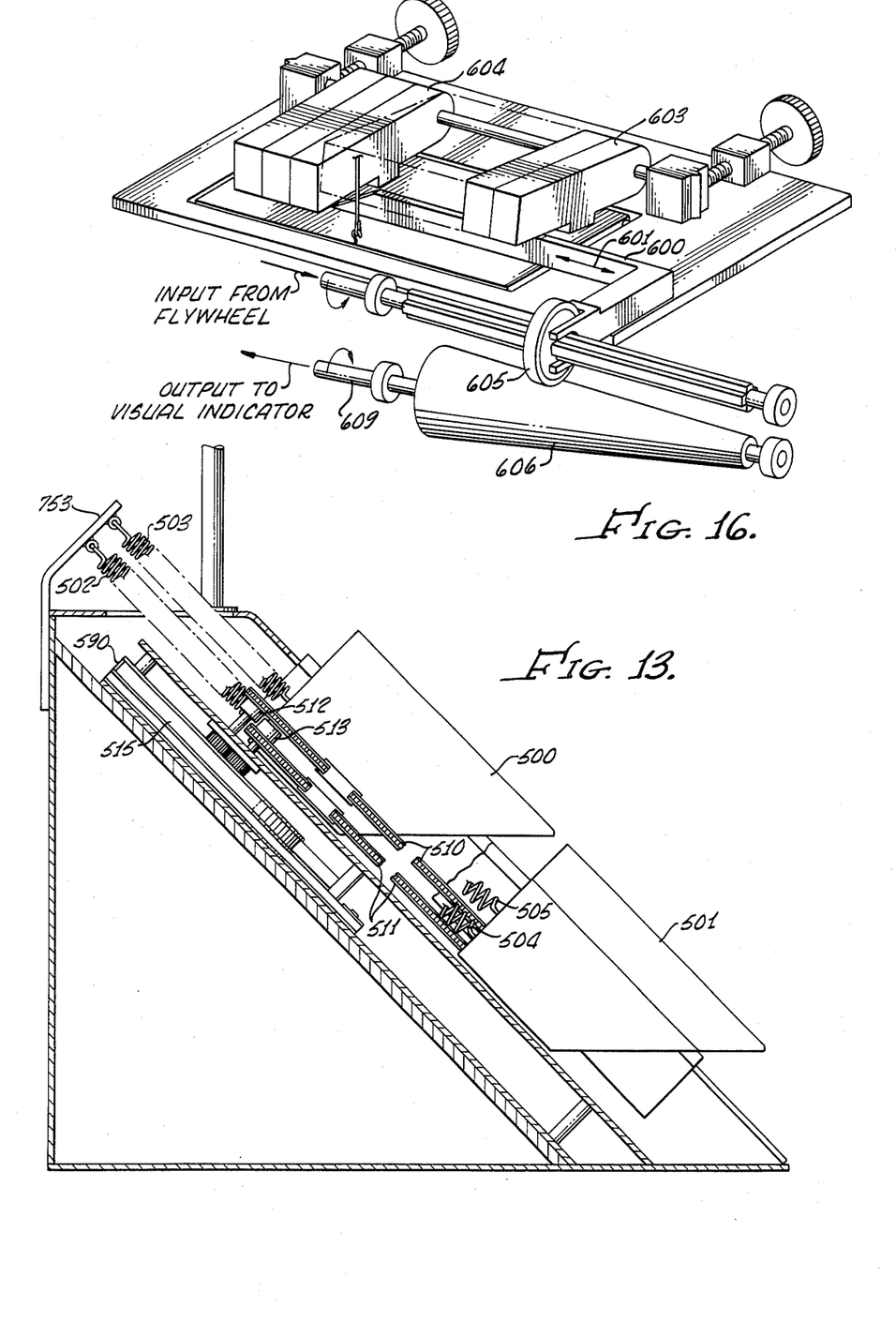
FIG. 13 shows a partial cross section relief view of the structure shown in FIG. 12 taken through a vertical plane parallel to the movement of the pedal platforms.
FIG. 16 shows the details of the mechanical rate incicator.
Figure 14:
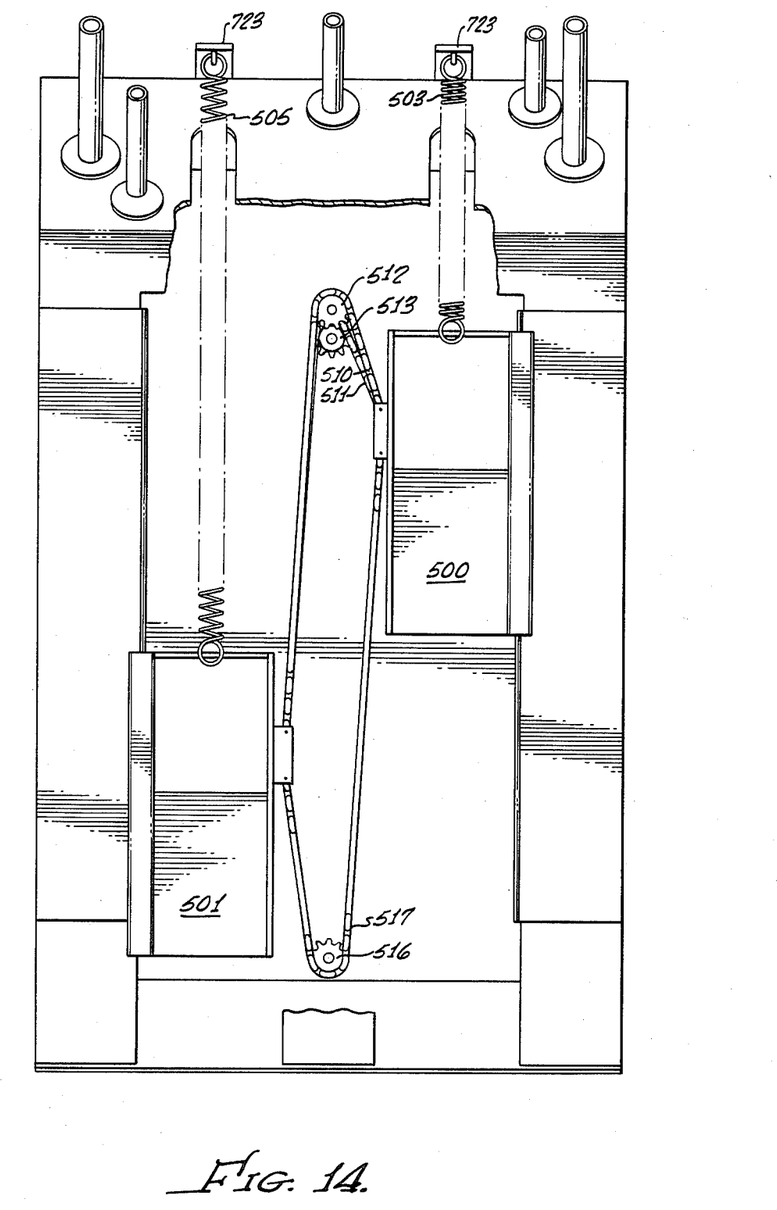
FIG. 14 shows a partial cutaway of the sloping top surface of FIG. 12 showing the details of the spring arrangement.

As shown in FIG. 13, the springs 504 and 505 are fully extended when the pedal platform 501 is near the bottom of its stroke while the springs 502 and 503 are only slightly extended because the pedal platform 500 is near the top of its stroke. FIG. 13 also shows chains 510-511 and ratchet clutches 512 513 which function as previously described in connection with the aforementioned embodiments to convert the reciprocal linear motion of the pedal platforms 500 and 501 into unidirectional rotary motion of flywheel 515. As shown in FIG. 14, the pedal platforms are also restrained by the idler 516 and chain 517, these elements serving the same function as 291 and 290 respectively as previously described in connection with the embodiment shown in FIG. 11.

Figure 15:
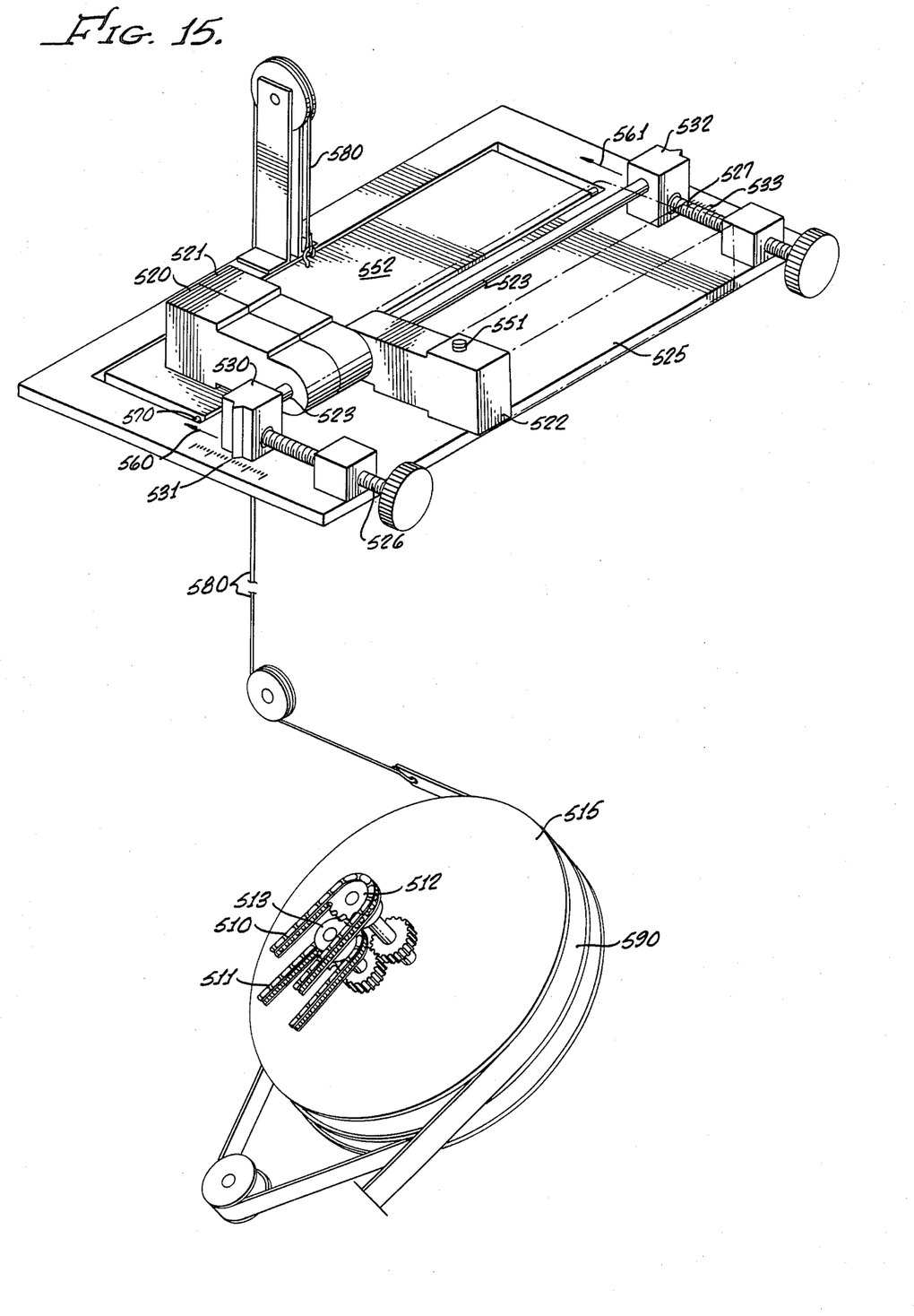
FIG. 15 shows a perspective view of the weight tray calibration system and loading arrangement.

FIG. 15 shows the details of the variable loading apparatus which comprises a weight assembly having a plurality of weights 520, 521, 522 which are mounted on a common rod 523. The rod 523 in turn is adjustably mounted for movement relative to platform 525 by screw shafts 526 and 527. The location of the rod 523 relative to the platform is indicated by pointers 530 and 532 which move relative to two marks 531 and 533 inscribed on the platform 525. Each weight is fashioned to have a protruding contact button (e.g., 551) so that it will engage weight door 552 at a single and determined point in accordance with the setting of screw shafts 526 and 527. When the screw shafts 526 and 527 are rotated clockwise, the pointers 530 and 532 move in the direction of the arrows 560 and 561 causing the rod 523 to be displaced in the same direction. When this occurs, those weights which are flipped over to the position shown by 520 and 521 will have their leverage point of contact relative to the bearing point 570 of weight door 552 increased. As a consequence, the force applied to cable 580 will increase, and the amount of drag applied to the flywheel 515 by the brake band 590 will also increase. Accordingly, if the markings 531 and 533 are properly scaled to represent a person's weight, the load steps can be varied to provide an exercise profile for example from 1 to 10 which is compensated to account for the weight of the operator. In the preferred embodiment, the exercise device will have the drag load scale calibrated such that at a scale setting of 10 the patient will require transfer of his entire weight to each step alternately to achieve a chosen rate of reciprocal motion or climb. Zero drag load corresponds to level walking. Equal load increments can then be added for gradual exercise from 0 to 1, 2, 3, etc. to 10. Because of this calibrated adjustment feature, a light weight person at all grade levels does not have to work against as heavy a drag load as a heavy person.

FIG. 16 shows a mechanical arrangement for measuring the energy output as a function of loading. When slide element 600 is moved in the direction as indicated by arrow 601, the wheel 605 is displayed to the conical element 606, thus varying the output rate at shaft 609 in proportion to the number of weights in contact with the weight door 552. Thus, as shown in the diagram, which corresponds to a small load, only two weights are in contact with the weight door 552. The wheel 605 is thus near the large end of the conical element 606 and the input from flywheel 515 rotates wheel 605 which in turn rotates element 606 at a speed which corresponds to a low rate of assent. Conversely, when slide element 600 is at the right most position, wheel 605 will be in contact with the narrow end of the conical element 606 and the output shaft 609 will rotate at maximum velocity for a given pedal speed.

The output shaft 609 may be coupled to any number of indicator devices to provide a visual and/or display. It will also be evident that electrical rate indicators as well as numerous other mechanical devices may be used in lieu of the particular mechanical arrangement depicted in FIG. 16. It will be further understood that all of the embodiments are exemplary only, and that the basic concepts and teachings of the invention are applicable to numerous alternate configurations or combinations thereof.

Thus although the invention has been shown and illustrated in the form of particular embodiments, it will be understood that these are not to be considered a limitation thereof and that numerous changes, modifications, and substitutions may be made without departing from the spirit of the invention.

I claim:

1. A stress testing device comprising:
   a base frame;
   a first pedal platform;
   first suspension means attached to said base frame and said first pedal platform for mounting said first pedal platform so as to permit said first pedal platform to translate at an inclined angle with respect to said base frame;
   a second pedal platform;
   second suspension means attached to said base frame and said second pedal platform for mounting said second pedal platform so as to permit said second pedal platform to translate at an inclined angle with respect to said base frame;
   a flywheel journeled to rotate with respect to said base frame;
   linkage means for connecting said first and second pedal platforms together so as to produce a reciprocal translational motion between said first and second pedal platforms;
   energy transfer means coupled to said linkage means and said flywheel for converting the reciprocal translation motion of said first and second pedal platforms into a unidirectional rotary motion of said flywheel;
   wherein said linkage means comprises a first chain having one end attached to said first pedal platform and having the other end attached to said second pedal platform, and a second chain having one end attached to said first pedal platform and having the other end attached to said second pedal platform and wherein said energy transfer means comprises a first ratchet sprocket journaled to rotate in a plane parallel to the plane of rotation of said flywheel and a second ratchet sprocket journaled to rotate in a plane parallel to the plane of rotation of said flywheel and wherein said first ratchet sprocket is positioned to engage said first chain and wherein said second ratchet sprocket is positioned to engage said second chain and coupling means for summing the output motion of said first and second ratchet sprockets whereby said motion will be coupled to said flywheel so as to cause said flywheel to be driven in the same direction when a force is applied to either pedal platform.

2. The apparatus recited in claim 1 wherein said coupling means comprises:
   a first gear attached to said first ratchet sprocket;
   a second gear attached to said second ratchet sprocket;
   mounting means for positioning said first and second gears so as to have their respective teeth in mesh whereby the motion produced by the movement of either ratchet sprocket will be summed.

3. The apparatus recited in claim 2 wherein said linkage means comprises:
   a first chain attached to one end of said first pedal platform and at the other end of said second pedal platform, and wherein said first chain engages said first ratchet sprocket, and;
   a second chain attached to one end to said first pedal platform and at the other end to said second panel platform and wherein said second chain engages said second ratchet sprocket.

4. The apparatus recited in claim 3 wherein said first suspension means comprises:
   a first set of upper guide wheels;
   a first set of lower guide wheels;
   an elongated member having a cross section adapted to ride in contact with the circumferential surface of said first set of upper and said first set of lower guide wheels;
   means for attaching said elongated member to said first pedal platform.

5. The apparatus recited in claim 4 wherein said first and second set of upper guide wheels are positioned so as to permit said elongated member to translate at an inclined angle.

6. The apparatus recited in claim 3 wherein said first suspension means comprises:
   an elongated channel member having a pair of protruding length uses parallel lips;
   a car having at least one set of upper wheels and at least one set of lower wheels, and wherein said set of upper wheels are spaced to ride on the upper surface of said elongated channel member and said lower wheels are spaced to ride in contact with the lower surface of said parallel lips.

7. The apparatus recited in claim 1 wherein said first suspension means comprises a bifilar suspension having first and second bifilar links of equal separation journal mounted to said base frame and said first pedal platform and wherein said second suspension means comprises a bifilar suspension having third and fourth bifilar links of equal length and equal separation journal mounted to said base frame and said second pedal platform.

8. The apparatus recited in claim 7 including an upright frame attached to said base frame, and further including:
   a friction belt positionally located with respect to said flywheel so as to contact the rim of said flywheel;
   means for applying a force to said friction belt so as to increase the frictional force of the belt against the rim of said flywheel.

9. A stress testing device comprising;
   a base frame;
   a first pedal platform;
   first suspension means attached to said base frame and said first pedal platform for mounting said first pedal platform so as to permit said first pedal platform to translate at an inclined angle with respect to said base frame;
   a second pedal platform;
   second suspension means attached to said base frame and said second pedal platform for mounting said second pedal platform so as to permit said second pedal platform to translate at an inclined angle with respect to said base frame;
a flywheel journeled to rotate with respect to said base frame;
linkage means for connecting said first and second pedal platforms together so as to produce a reciprocal translational motion between said first and second pedal platforms;
energy transfer means coupled to said linkage means and said flywheel for converting the reciprocal translational motion of said first and second pedal platforms into a unidirectional rotary motion of said flywheel; and
wherein said flywheel is mounted so as to rotate in a vertical plane when the plane of said base frame is horizontal and wherein said energy transfer means comprises first and second ratchet sprockets having output shafts which are axially coupled to said flywheel for unidirectionally summing the output motion of said flywheel.

10. The apparatus recited in claim 9 wherein said linkage means comprises:
a first chain attached to one end of said first pedal platform and at the other end of said second pedal platform, and wherein said first chain engages said first ratchet sprocket, and;
a second chain attached to one end to said first pedal platform and at the other end to said second pedal platform and wherein said second chain engages said second ratchet sprocket.

11. A stress test exercise device comprising:
a base frame;
a first pedal platform;
first suspension means attached to said base frame and said first pedal platform for mounting said first pedal platform so to permit said first pedal platform to translate at an inclined angle with respect to said base frame;
a second pedal platform;
second suspension means attached to said base frame and said second pedal platform for mounting said second pedal platform so as to permit said second pedal platform to translate at an inclined angle with respect to said base frame;
a flywheel journaled to rotate with respect to said base frame;
linkage means for connecting said first and second pedal platforms together so as to produce a reciprocal translational motion between said first and second pedal platforms;
energy transfer means coupled to said linkage means and said flywheel for converting the reciprocal translational motion of said first and second pedal platforms into a unidirectional rotary motion of said flywheel;
wherein said linkage means comprises a first chain having one end attached to said first pedal platform and having the other end attached to said second pedal platform, and a second chain having one end attached to said first pedal platform and having the other end attached to said second pedal platform and wherein said energy transfer means comprises a first ratchet sprocket journeled to rotate in a plane parallel to the plane of rotation of said flywheel and a second ratchet sprocket journeled to rotate in a plane parallel to the plane of rotation of said flywheel and wherein said first ratchet sprocket is positioned to engage said first chain and wherein said second ratchet sprocket is positioned to engage said second chain and coupling means for summing the output motion of said first and second ratchet sprockets whereby said motion will be coupled to said flywheel so as to cause said flywheel to be driven in the same direction when a force is applied to either pedal platform and;
energy storage means comprising at least one resilient member attached to said first and and second pedal platforms for accelerating the ascent of said pedal platforms.

12. The apparatus recited in claim 11 wherein said energy storage means comprises at least one spring.

13. The apparatus recited in claim 11 including loading means for varying the drag on said flywheel.

14. The apparatus recited in claim 13 wherein said means for varying the drag on said flywheel comprises:
a platform;
a weight tray pivotally mounted to said platform;
at least one weight;
means for pivotally mounting said weight on said platform;
means for moving the pivot point of said weight so as to vary the contact position of said weight relative to said weight tray, thereby varying the effective weight disposed on said weight tray;
braking means for applying a frictional restraint to the periphery of said flywheel;
coupling means connecting said weight tray to said braking means whereby the braking force of said braking means will be functionally dependent upon the location of the pivot point of said weight.

15. The apparatus recited in claim 14 including means for indicating the rate of climb as a function of platform pedal velocity and braking force.

16. The apparatus recited in claim 13 wherein said means for varying the drag on said flywheel comprises:
adjustable loading means for varying the frictional drag on said flywheel in accordance with the applied load;
indicator means responsively coupled to said adjustable loading means for relating the magnitude of the applied load to the magnitude of the frictional force required to produce a given flywheel drag.

17. The apparatus recited in claim 16 wherein said indicator means is scaled so as to indicate the amount of load necessary to provide a drag force which will compensate for the weight of the operator.

18. The apparatus recited in claim 17 wherein said scaling of said indicator means is such that the maximum output velocity of the flywheel will be the same for all persons irrespective of weight when said adjustable loading means is set so as to cause said indicator means to correspond with the weight of the operator.

19. The apparatus recited in claim 18 including incremental load means for varying the amount of load applied to the flywheel in steps which are multiples of the maximum load for each individual's weight.

20. The apparatus recited in claim 19 including:
measuring means responsively coupled to said incremental load means for totaling the comulative output energy for each incremental load over a given time period to provide an exercise profile.

* * * * *